(12) United States Patent
Merrell et al.

(10) Patent No.: US 9,278,002 B2
(45) Date of Patent: Mar. 8, 2016

(54) ELBOW ANTIBIOTIC SPACER IMPLANT

(71) Applicants: Gregory Merrell, Zionsville, IN (US); Jeffrey Michael Bradley, Carmel, IN (US)

(72) Inventors: Gregory Merrell, Zionsville, IN (US); Jeffrey Michael Bradley, Carmel, IN (US)

(*) Notice: Subject to any disclaimer, the term of this patent is extended or adjusted under 35 U.S.C. 154(b) by 21 days.

(21) Appl. No.: 14/297,973

(22) Filed: Jun. 6, 2014

(65) Prior Publication Data

US 2014/0364954 A1 Dec. 11, 2014

Related U.S. Application Data

(60) Provisional application No. 61/832,228, filed on Jun. 7, 2013.

(51) Int. Cl.
*A61F 2/38* (2006.01)
*A61F 2/30* (2006.01)

(52) U.S. Cl.
CPC ..... *A61F 2/3804* (2013.01); *A61F 2002/30462* (2013.01); *A61F 2002/30672* (2013.01); *A61F 2002/30677* (2013.01); *A61F 2310/00353* (2013.01)

(58) Field of Classification Search
CPC ........... A61F 2/38; A61F 2/40; A61F 2/3804; A61F 2/3809; A61F 2002/30723; A61F 2002/30724; A61F 2002/30677; A61F 2002/30667; A61F 2002/30672; A61F 2002/3809; A61F 2002/3813; A61F 2002/3818; A61F 2002/3822; A61F 2002/3831; A61F 2310/00353; A61F 2310/00359; A61F 2/3836
USPC ................................ 623/20.11–20.13, 20.14
See application file for complete search history.

(56) References Cited

U.S. PATENT DOCUMENTS

| | | | | | |
|---|---|---|---|---|---|
| 3,882,858 | A | * | 5/1975 | Klemm | A61K 9/0024 606/76 |
| 4,274,163 | A | * | 6/1981 | Malcom | A61B 17/8808 606/94 |
| 4,399,814 | A | * | 8/1983 | Pratt, Jr. | A61B 17/8808 606/94 |
| 4,488,549 | A | * | 12/1984 | Lee | A61B 17/8808 606/94 |
| 4,711,233 | A | * | 12/1987 | Brown | A61B 17/8802 606/81 |
| 4,888,024 | A | * | 12/1989 | Powlan | A61B 17/8808 623/23.19 |
| 4,892,550 | A | * | 1/1990 | Huebsch | A61F 2/4637 623/23.19 |
| 5,085,861 | A | * | 2/1992 | Gerhart | A61L 24/0015 424/423 |
| 5,116,377 | A | * | 5/1992 | Skripitz | A61F 2/30728 623/23.19 |
| 5,133,767 | A | * | 7/1992 | Frey | A61B 17/8808 623/23.54 |
| 5,133,771 | A | * | 7/1992 | Duncan | A61F 2/30942 264/DIG. 30 |
| 5,133,772 | A | * | 7/1992 | Hack | A61F 2/36 623/23.19 |
| 5,156,606 | A | * | 10/1992 | Chin | A61B 17/1628 606/100 |
| 5,217,493 | A | * | 6/1993 | Raad | A61K 31/65 604/265 |
| 5,258,420 | A | * | 11/1993 | Posey-Dowty | A61L 24/001 424/78.18 |
| 5,290,291 | A | * | 3/1994 | Linden | A61B 17/8847 606/86 R |
| 5,340,362 | A | * | 8/1994 | Carbone | A61F 2/30723 606/95 |

(Continued)

*Primary Examiner* — Alvin Stewart
(74) *Attorney, Agent, or Firm* — Occhiuti & Rohlicek LLP

(57) ABSTRACT

An articulable elbow spacer includes a humeral component, an ulnar component, and a tie. The humeral component includes a proximal end having a rod for insertion into a humeral canal and a distal end including a first joint member, the first joint member including antibiotic cement and one or more tunnels. The ulnar component includes a proximal end including a second joint member, the second joint member including antibiotic cement and including one or more tunnels, and configured to receive the first joint member and a distal end having a rod for insertion into an ulnar canal. The tie is configured to link the humeral component to the ulnar component and is configured for insertion into the one or more tunnels of the first joint member and the one or more tunnels of the second joint member.

15 Claims, 10 Drawing Sheets

(56) References Cited

U.S. PATENT DOCUMENTS

| | | | | |
|---|---|---|---|---|
| 5,376,123 | A * | 12/1994 | Klaue | A61B 17/8841 623/23.19 |
| 5,433,718 | A * | 7/1995 | Brinker | A61B 17/72 606/92 |
| 5,501,687 | A * | 3/1996 | Willert | A61B 17/8808 606/92 |
| 5,514,137 | A * | 5/1996 | Coutts | A61B 17/7098 606/62 |
| 5,554,111 | A * | 9/1996 | Morrey | A61M 1/0084 433/29 |
| 5,562,736 | A * | 10/1996 | Ray | A61B 17/1604 606/184 |
| 5,571,204 | A * | 11/1996 | Nies | A61F 2/30723 623/23.19 |
| 5,681,289 | A * | 10/1997 | Wilcox | A61B 17/60 604/175 |
| 5,702,446 | A * | 12/1997 | Schenck | A61F 2/30907 433/226 |
| 5,725,596 | A * | 3/1998 | Burke | A61B 17/1659 623/23.21 |
| 5,728,395 | A * | 3/1998 | Ohtsuka | A61F 2/28 264/102 |
| 5,741,265 | A * | 4/1998 | Chan | A61B 17/8808 606/92 |
| 5,755,811 | A * | 5/1998 | Tanamal | A61B 2/367 623/23.35 |
| 5,827,289 | A * | 10/1998 | Reiley | A61B 10/025 606/191 |
| 5,938,698 | A * | 8/1999 | Sandoz | A61F 2/30724 623/16.11 |
| 5,954,771 | A * | 9/1999 | Richelsoph | A61F 2/30723 623/23.15 |
| 5,980,573 | A * | 11/1999 | Shaffner | A61F 2/36 128/898 |
| 6,066,154 | A * | 5/2000 | Reiley | A61B 17/7097 606/192 |
| 6,113,639 | A * | 9/2000 | Ray | A61F 2/4684 623/17.16 |
| 6,155,812 | A * | 12/2000 | Smith | A61F 2/30942 249/141 |
| 6,217,619 | B1 * | 4/2001 | Keller | A61F 2/28 623/20.14 |
| 6,248,110 | B1 * | 6/2001 | Reiley | A61B 10/025 606/192 |
| 6,361,731 | B1 * | 3/2002 | Smith | A61F 2/30942 264/271.1 |
| 6,423,083 | B2 * | 7/2002 | Reiley | 604/96.01 |
| 6,447,514 | B1 * | 9/2002 | Stalcup | A61B 17/164 606/96.01 |
| 6,485,754 | B1 * | 11/2002 | Wenz | A61L 24/0015 424/405 |
| 6,497,901 | B1 * | 12/2002 | Royer | A61K 9/0024 424/423 |
| 6,544,472 | B1 * | 4/2003 | Compton | A61F 2/30767 419/2 |
| 6,679,890 | B2 * | 1/2004 | Margulies | A61B 17/742 606/60 |
| 6,740,090 | B1 * | 5/2004 | Cragg | A61B 17/1617 128/898 |
| 6,921,403 | B2 * | 7/2005 | Cragg | A61B 17/1671 606/246 |
| 6,969,404 | B2 * | 11/2005 | Ferree | A61B 17/1671 623/17.11 |
| 6,989,033 | B1 * | 1/2006 | Schmidt | A61F 2/44 623/23.51 |
| 7,112,205 | B2 * | 9/2006 | Carrison | A61B 17/3472 606/92 |
| 7,141,053 | B2 * | 11/2006 | Rosa | A61B 17/155 606/86 R |
| 7,211,113 | B2 * | 5/2007 | Zelener | A61F 2/32 623/22.43 |
| 7,250,055 | B1 * | 7/2007 | Vanderwalle | A61B 17/7098 606/71 |
| 7,255,713 | B2 * | 8/2007 | Malek | A61B 17/7061 606/99 |
| 7,601,157 | B2 * | 10/2009 | Boyd | A61B 17/8805 606/90 |
| 7,789,646 | B2 * | 9/2010 | Haney | A61F 2/30942 249/158 |
| 7,862,619 | B2 * | 1/2011 | Clark | A61F 2/38 623/20.3 |
| 7,914,585 | B2 * | 3/2011 | Keller | A61F 2/30771 623/22.11 |
| 8,038,682 | B2 * | 10/2011 | McGill et al. | A61B 17/8816 606/94 |
| 8,454,706 | B2 * | 6/2013 | de Beaubien | A61F 2/36 623/23.99 |
| 8,652,216 | B2 * | 2/2014 | Chen | A61B 17/3468 623/23.72 |
| 8,673,018 | B2 * | 3/2014 | Walls | A61K 33/38 623/23.57 |
| 8,801,983 | B2 * | 8/2014 | Haney | A61F 2/30942 249/158 |
| 8,900,322 | B2 * | 12/2014 | de Beaubien | A61F 2/36 623/23.39 |
| 8,900,323 | B2 * | 12/2014 | de Beaubien | A61F 2/36 623/23.39 |
| 8,920,152 | B2 * | 12/2014 | Hawkins | 249/161 |
| 8,974,538 | B2 * | 3/2015 | Teeny | A61F 2/38 606/60 |
| 2003/0060891 | A1 * | 3/2003 | Shah | A61F 2/30728 623/22.13 |
| 2003/0097184 | A1 * | 5/2003 | Mitsugi | A61B 17/8802 623/23.19 |
| 2003/0163205 | A1 * | 8/2003 | Lawson | A61F 2/30723 623/23.48 |
| 2003/0187513 | A1 * | 10/2003 | Durniak | A61B 17/8802 623/22.12 |
| 2004/0013703 | A1 * | 1/2004 | Ralph | A61M 31/002 424/426 |
| 2004/0036189 | A1 * | 2/2004 | Ensign | A61F 2/30942 264/40.1 |
| 2004/0054417 | A1 * | 3/2004 | Soffiati | A61F 2/38 623/20.31 |
| 2004/0064192 | A1 * | 4/2004 | Bubb | A61F 2/46 623/23.5 |
| 2004/0225360 | A1 * | 11/2004 | Malone | A61B 17/7064 623/17.11 |
| 2005/0021084 | A1 * | 1/2005 | Lu | A61B 17/864 606/218 |
| 2005/0025807 | A1 * | 2/2005 | Ootsuka | A61K 9/0024 424/426 |
| 2005/0107885 | A1 * | 5/2005 | Evans | A61F 2/30942 623/20.21 |
| 2005/0187555 | A1 * | 8/2005 | Biedermann | A61B 17/68 606/62 |
| 2006/0004431 | A1 * | 1/2006 | Fuller | A61B 17/86 607/116 |
| 2006/0014120 | A1 * | 1/2006 | Sapian | A61C 8/0057 433/173 |
| 2006/0093646 | A1 * | 5/2006 | Cima | A61C 8/0012 424/425 |
| 2007/0005142 | A1 * | 1/2007 | Rhodes | A61F 2/389 623/20.32 |
| 2007/0162132 | A1 * | 7/2007 | Messerli | A61B 17/68 623/17.11 |
| 2007/0213835 | A1 * | 9/2007 | Wimmer | A61F 2/30 623/23.58 |
| 2007/0222114 | A1 * | 9/2007 | Ziran | A61F 2/30942 264/279 |
| 2007/0254008 | A1 * | 11/2007 | Rubsamen | A61K 9/0024 424/423 |
| 2008/0058950 | A1 * | 3/2008 | Leonard | A61F 2/30 623/22.4 |
| 2008/0286377 | A1 * | 11/2008 | Healey | A61K 31/683 424/501 |
| 2009/0069899 | A1 * | 3/2009 | Klein | A61F 2/36 623/22.4 |
| 2009/0130167 | A1 * | 5/2009 | Shelton | A61F 2/30721 424/423 |
| 2009/0146342 | A1 * | 6/2009 | Haney | A61F 2/30942 264/250 |
| 2009/0157189 | A1 * | 6/2009 | Hartman | A61F 2/30 623/18.11 |

(56) References Cited

U.S. PATENT DOCUMENTS

| | | | |
|---|---|---|---|
| 2009/0175978 A1* | 7/2009 | Hawkins | B28B 23/024 425/214 |
| 2010/0042167 A1* | 2/2010 | Nebosky | A61B 17/7061 606/315 |
| 2010/0042214 A1* | 2/2010 | Nebosky | A61B 17/56 623/16.11 |
| 2010/0042215 A1* | 2/2010 | Stalcup | A61B 17/68 623/16.11 |
| 2010/0049322 A1* | 2/2010 | McKay | A61F 2/30756 623/16.11 |
| 2010/0068243 A1* | 3/2010 | Khairoun | A61L 24/0036 424/426 |
| 2010/0069469 A1* | 3/2010 | Young | A61K 6/033 514/44 R |
| 2010/0102484 A1* | 4/2010 | Haney | A61F 2/30942 264/328.1 |
| 2010/0152319 A1* | 6/2010 | Shalaby | A61K 9/5026 523/117 |
| 2010/0178250 A1* | 7/2010 | Forbes | A61B 17/8802 514/1.1 |
| 2010/0217401 A1* | 8/2010 | de Beaubien | A61F 2/36 623/20.34 |
| 2010/0292803 A1* | 11/2010 | Giori | A61F 2/30942 623/20.14 |
| 2011/0071072 A1* | 3/2011 | Calderone | A61K 38/12 514/3.4 |
| 2011/0287064 A1* | 11/2011 | Vogt | A61L 27/28 424/400 |
| 2011/0311591 A1* | 12/2011 | Wang | A61L 27/34 424/400 |
| 2012/0164311 A1* | 6/2012 | Vogt | A61L 27/32 427/2.26 |
| 2012/0256344 A1* | 10/2012 | Stolarski | A61F 2/30942 264/251 |
| 2012/0290096 A1* | 11/2012 | Messerli | A61B 17/68 623/17.16 |
| 2013/0041472 A1* | 2/2013 | Rabiner | A61B 17/7275 623/18.11 |
| 2013/0150979 A1* | 6/2013 | Schindler | A61L 27/16 623/23.62 |
| 2013/0173014 A1* | 7/2013 | Mikos | A61L 27/16 623/23.63 |
| 2013/0187310 A1* | 7/2013 | Vogt | A61F 2/36 264/313 |
| 2013/0289721 A1* | 10/2013 | Klebuc | A61F 2/12 623/8 |
| 2013/0295213 A1* | 11/2013 | Lomicka | A61F 2/3094 425/150 |
| 2014/0159282 A1* | 6/2014 | Smith | A61F 2/30942 264/328.7 |
| 2014/0274971 A1* | 9/2014 | McGee | A61K 47/48992 514/152 |
| 2014/0277532 A1* | 9/2014 | Teeny | A61F 2/38 623/20.24 |
| 2014/0328902 A1* | 11/2014 | Johnson | A61K 8/14 424/450 |
| 2014/0343560 A1* | 11/2014 | Vogt | A61B 17/8811 606/92 |
| 2014/0348973 A1* | 11/2014 | Holt | A61F 2/36 425/542 |
| 2014/0364954 A1* | 12/2014 | Merrell | A61F 2/3804 623/20.12 |
| 2015/0001765 A1* | 1/2015 | Vogt | A61F 2/389 264/331.18 |
| 2015/0012105 A1* | 1/2015 | Kim | A61F 2/30965 623/20.28 |
| 2015/0134068 A1* | 5/2015 | Leonard | A61F 2/3886 623/20.27 |
| 2015/0250598 A1* | 9/2015 | Yakimicki | A61F 2/3609 623/20.35 |

* cited by examiner

ELBOW ANTIBIOTIC SPACER IMPLANT

CROSS-REFERENCE TO RELATED APPLICATIONS

The application claims the benefit of U.S. Provisional Application Ser. No. 61/832,228, filed Jun. 7, 2013, the content of which is incorporated herein by reference.

BACKGROUND

This invention relates to an antibiotic spacer element for treating deep infection about the elbow joint.

It is well accepted to use an antibiotic cement spacer in the treatment of deep infection following total elbow arthroplasty. Known descriptions of elbow devices for deep infection include static spacers meant to maintain the soft tissue envelope or space.

Conventional antibiotic cement elbow spacers generally include a piece of cement in each of the intramedullary canals including the humerus and ulna, as well as a block of cement between the two bones. This model allows for direct treatment or delivery of antibiotics to the humerus, ulna, and the soft tissue envelope previously affected by a deep infection. Motion is permitted but unstable and often requires full time splinting to allow for more stability and to control for pain during activities of daily living.

SUMMARY

A device for use as a total elbow antibiotic spacer is provided. The device includes two separate components, which can be linked together to create the final two-piece articulating total elbow spacer. The device includes a component configured to fit into the distal end of the humerus as well as a component configured to fit into the proximal ulna. The components are fabricated using antibiotic cement.

In some examples, deep infection following total elbow arthroplasty requires the removal of both the humeral and ulnar components of the elbow to aid in clearance of the infection. Prior to re-implantation of a conventional metal total elbow arthroplasty, the elbow is treated with an antibiotic spacer. This device includes a standard sized humeral and ulnar component that can be cemented into any elbow and provide for an articulating surface for motion.

In some examples, such components can be made from plastic molds which are resistant to the heat of curing cement.

The humeral component may include one or more of the following features:

The design of the humeral component may be based off of the normal anatomy of an adult distal humerus and may include a solid piece of antibiotic bone cement. In general, the normal adult anatomy of the medial trochlea is utilized. The articulating portion of this device may be made from mirror images of the medial trochlea linked together. This allows for a deep groove, which acts as a simple hinge against the ulnar component. The final articular surface may have a substantially hourglass appearance and shape.

A single drill hole may be included above the articular surface in what would represent the coronoid and olecranon fossa of the distal humerus. The drill hole creates a short tunnel which passes from an anterior side to a posterior side of the device and may be located at the midline of the device to allow for a central linkage point between the humeral and ulnar components.

The ulnar component may include one or more of the following features:

The ulnar component may be composed of a solid piece of antibiotic bone cement. The component may be designed as a negative mold of the distal end of the humeral component. This creates a highly conformed hinge joint. The ulnar component may include a coronoid and olecranon process, which articulate with the distal aspect of the humeral component. They also aid in stability by prevention deep flexion and full extension of the elbow joint.

In some examples, there are two distinct tunnels in the ulnar component which aid in linkage to the humeral component. The first tunnel begins at the tip of the coronoid process and exits obliquely at the base of the ulnar component on the side. The second tunnel begins at the tip of the olecranon process and exits obliquely at the base of the ulnar component on the side. The start of each tunnel may be in the midline of the device, while the end to each tunnel exits on the same side of the ulnar component at its base. The feature allows for a central axis for linkage between the humeral and ulnar components.

The linkage between the humeral and ulnar components may include one or more of the following features:

After the two components are brought into tight apposition, they form a highly congruent simple hinge joint. Stabile articulation requires linkage between the two components. The tunnel position in the humeral and ulnar components is critical to successful linkage. The tunnels form a circular pattern, which allows for a stabile smooth range of motion. In some examples, the two components are linked with a tie system (e.g., a ropes, zip tie, cable, thread, string, wire, or the like) under appropriate tension to provide stability as well as to allow for motion.

The intramedullary rods may include one or more of the following features:

The rods are an essential part to the design of the humeral and ulnar components. The rods add rotational stability to the components once they are implanted in the humeral and ulnar shafts. In some examples, the rods are placed in the central axis of the humeral and ulnar shafts. The rods can also be used to help remove the components prior to re-implantation with a standard metal total elbow athroplasty.

The humeral and ulnar molds may include one or more of the following features:

The molds may be two-piece casts of the humeral and ulnar components. The molds may be heat stable to curing cement and allow for identical replication of each component.

Embodiments may include one or more of the following important features.

The design of the humeral component may be based on the native anatomy of the human adult medial trochlea of the distal humerus. The diameter and radius of curvature of the medial trochlea of the distal humerus may be mimicked. The anterior side of the humeral component may be a mirror image of the posterior side of the humeral component. The distal aspect may be based on mirror images of the medial side of the trochlea, which may then be fused to create a deep groove to form the basis of a simple gingylmus hinge design. The proximal shaft may taper to meet a humeral intramedullary rod.

The humeral component may be made from antibiotic bone cement. The design of the ulnar component may be a reverse or negative of the distal end of the humeral component. The proximal ulnar component may articulate with the humeral component to create a simple ginglymus hinge joint (i.e., a hinge joint that allows motion in only a single plane). The ulnar component may match the normal proximal ulnar anatomy with a coronoid anteriorly as well as an olecranon posteriorly. The distal shaft of the ulnar component may taper to meet an ulnar intramedullary rod, where the rod may be placed on the most posterior aspect of the ulnar component. The humeral component and the ulnar component may be linked via a tie system to allow for range of motion.

The humeral component may have a tunnel placed centrally just above the groove between the two reflected medial trochleas. The ulnar component may have tunnels, which are placed at the tip of the coronoid and olecranon respectively. The posterior hole at the base of the coronoid and olecranon may be positioned on the same side. The combined linkage between the humeral component and the ulnar component may match a circular pattern. The humeral component and the ulnar component may have a centrally placed rod.

The humeral component and the ulnar component may be made from molds that are reusable and match the final components.

In another general aspect, an articulable elbow spacer includes a humeral component, an ulnar component, and a tie. The humeral component includes a proximal end having a rod for insertion into a humeral canal and a distal end including a first joint member, the first joint member including antibiotic cement and one or more tunnels. The ulnar component includes a proximal end including a second joint member, the second joint member including antibiotic cement and including one or more tunnels, and configured to receive the first joint member and a distal end having a rod for insertion into an ulnar canal. The tie is configured to link the humeral component to the ulnar component and is configured for insertion into the one or more tunnels of the first joint member and the one or more tunnels of the second joint member.

Aspects may include one or more of the following features.

The first joint member may include a groove and the second joint member may include a ridge configured to be received by the groove. The first joint member may include a first medial trochlea shaped portion fused to a second medial trochlea shaped portion, the first medial trochlea shaped portion and the second medial trochlea shaped portion defining the groove. The first medial trochlea shaped portion may be a reflection of the second medial trochlea shaped portion. The groove may be a substantially V-shaped groove. The groove may include an inner surface having a first inner surface wall and a second inner surface wall opposing the first inner surface wall. The first inner surface wall may have a convex shape and the second inner surface wall may have a convex shape.

The ulnar component may include a coronoid process and an olecranon process for limiting a range of articulation of the articulable elbow spacer. The coronoid process may protrudes further from the ulnar component in an anterior direction than the olecranon process. The tie may have a circular shape and the one or more tunnels of the distal end of the joint member and the one or more tunnels of the proximal end of the second joint member may form a circular tunnel pattern configured to receive the tie. The humeral component and the ulnar component may form a ginglymus hinge. The first joint member may include a tapered portion tapering along a direction from the distal end of the humeral component to the proximal end of the humeral component. The second joint member may include a tapered portion tapering along a direction from the proximal end of the ulnar component to the distal end of the ulnar component.

A thinnest portion of the humeral component may have a thickness in a range of 1 mm to 3 mm. The thinnest portion of the humeral component may have a thickness of 2 mm. The rod for insertion into the humeral canal may have a diameter of 3/16 of an inch. The rod for insertion into the ulnar canal may have a diameter of 1/8 of an inch.

In another general aspect, a method for fabricating an articulable elbow spacer includes forming a humeral component, forming an ulnar component, and linking the humeral component and the ulnar component. Forming the humeral component includes providing a first joint member mold, pouring antibiotic cement into the first joint member mold, placing a first rod into the antibiotic cement in the first joint member mold, curing the antibiotic cement, and forming one or more tunnels in the antibiotic cement. Forming a ulnar component includes providing a second joint member mold, pouring antibiotic cement into the second joint member mold, placing a second rod into the antibiotic cement in the second joint member mold, curing the antibiotic cement, and forming one or more tunnels in the antibiotic cement. To link the humeral component to the ulnar component a tie is provided and is inserted into the one or more tunnels of the humeral component and inserting the tie into the one or more tunnels of the ulnar component.

Aspects may include one or more of the following features.

Forming the one or more tunnels in the antibiotic cement of the humeral component may include drilling the one or more tunnels into the antibiotic cement of the humeral component and forming the one or more tunnels in the antibiotic cement of the ulnar component may include drilling the one or more tunnels into the antibiotic cement of the ulnar component.

Forming the humeral component including curing the antibiotic cement may include heating the first joint member mold to a curing temperature of the antibiotic cement, wherein the curing temperature is less than a melting temperature of a material of the first joint member mold. Forming the ulnar component including curing the antibiotic cement may include heating the second joint member mold to a curing temperature of the antibiotic cement, wherein the curing temperature is less than a melting temperature of a material of the second joint member mold.

Embodiments may include one or more of the following advantages.

Among other advantages, the antibiotic cement elbow spacer provides antibiotic elution while allowing for a stable linked range of motion.

Other features and advantages of the invention are apparent from the following description, and from the claims.

DESCRIPTION OF DRAWINGS

FIG. 6a is a perspective view of the obliquely oriented tunnels in the tip of the coronoid and olecranon process.

FIG. 6b is a lateral perspective of the ulnar component and shows the exit on the side of the component of the coronoid and olecranon tunnels of FIG. 6a.

DESCRIPTION

Figure 1:
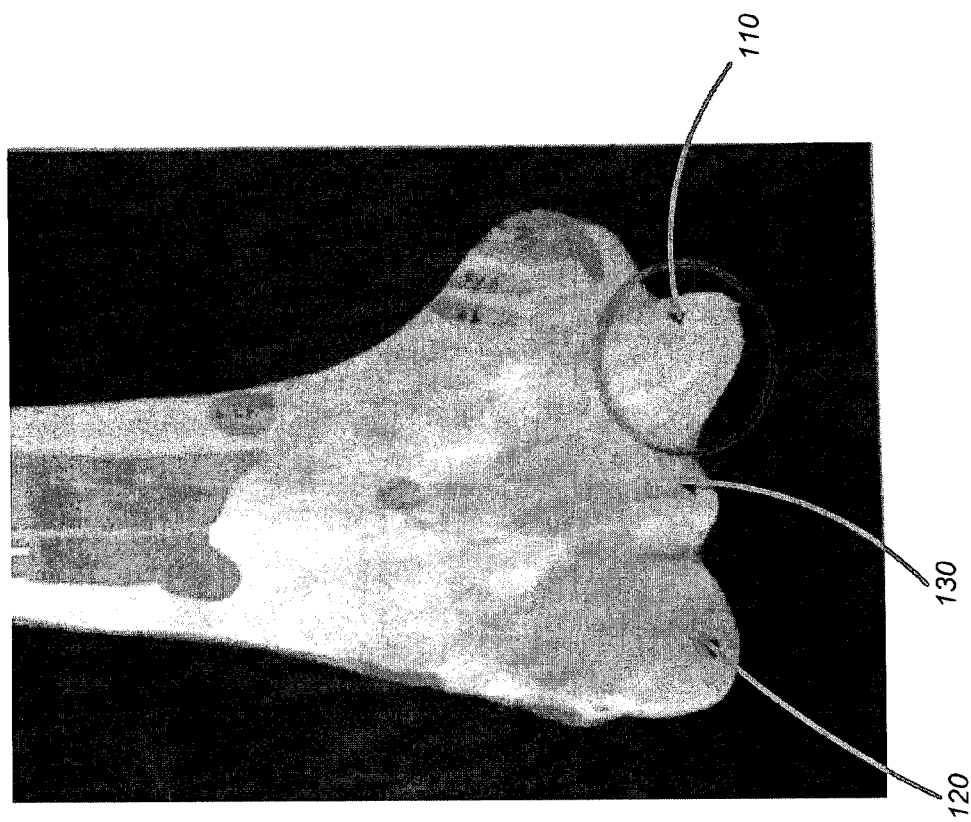
FIG. 1 is an anterior view of a plastic replica of an adult right distal humerus. The medial portion of the trochlea is used as the basic design of the humeral component of FIG. 2.

Referring to FIG. 1, an anterior prospective of an adult right distal humerus 105 is shown. The anterior portion of the capitellum 120, lateral trochlea 130, and medial trochlea 110 is shown. The medial trochlea 110 is used as the basic design of a humeral component seen in FIGS. 2a and 2b.

Figures 2A, 2B:
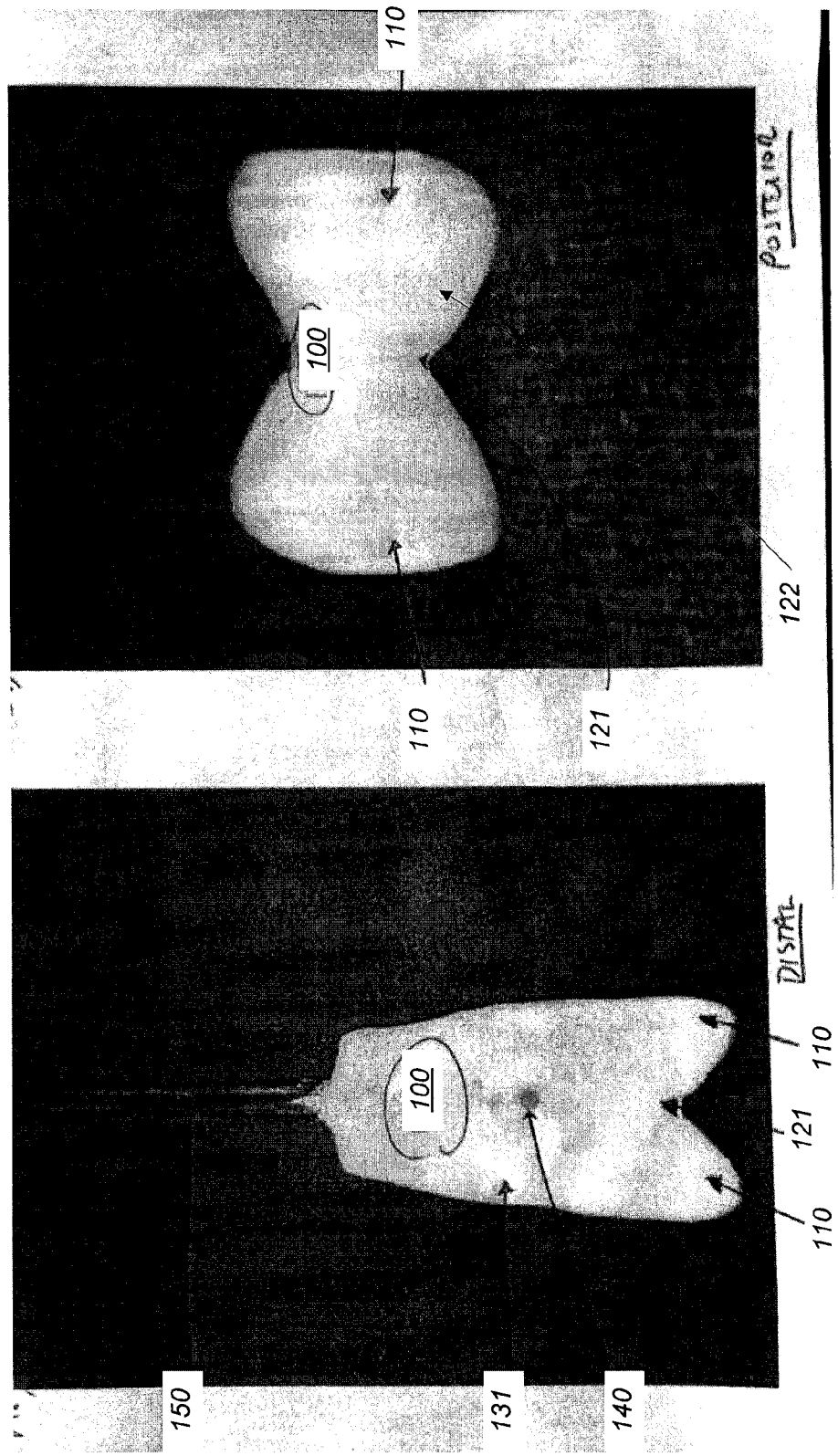
FIG. 2a is a humeral component. The anterior view shows the hourglass appearance of the articular surface.
FIG. 2b is the articular surface of the distal humeral component, which is a simple mirror image of the medial trochlea of FIG. 1.

Referring to FIG. 2a, an anterior view of the humeral component 100 is shown. The distal aspect of the humeral component 100 is composed of fused mirror images of the medial trochlea 110 seen in FIG. 1. The fusion between the medial trochleas 110, forms a deep groove 121. The body of the humeral component 131 connects the distal articular surface 122 to humeral rods 150. There is a central tunnel 140 in the body 131 used for humeral linkage.

Referring to FIG. 2b, a view of the distal articular surface 122 of the humeral component 100 is shown. The articular surface 122 shows the relationship between the fused medial trochlear pieces 110 and the central groove 121. In general the anterior to posterior dimension of the medial trochlea 110 is twice that of the central groove 121.

Figure 3:
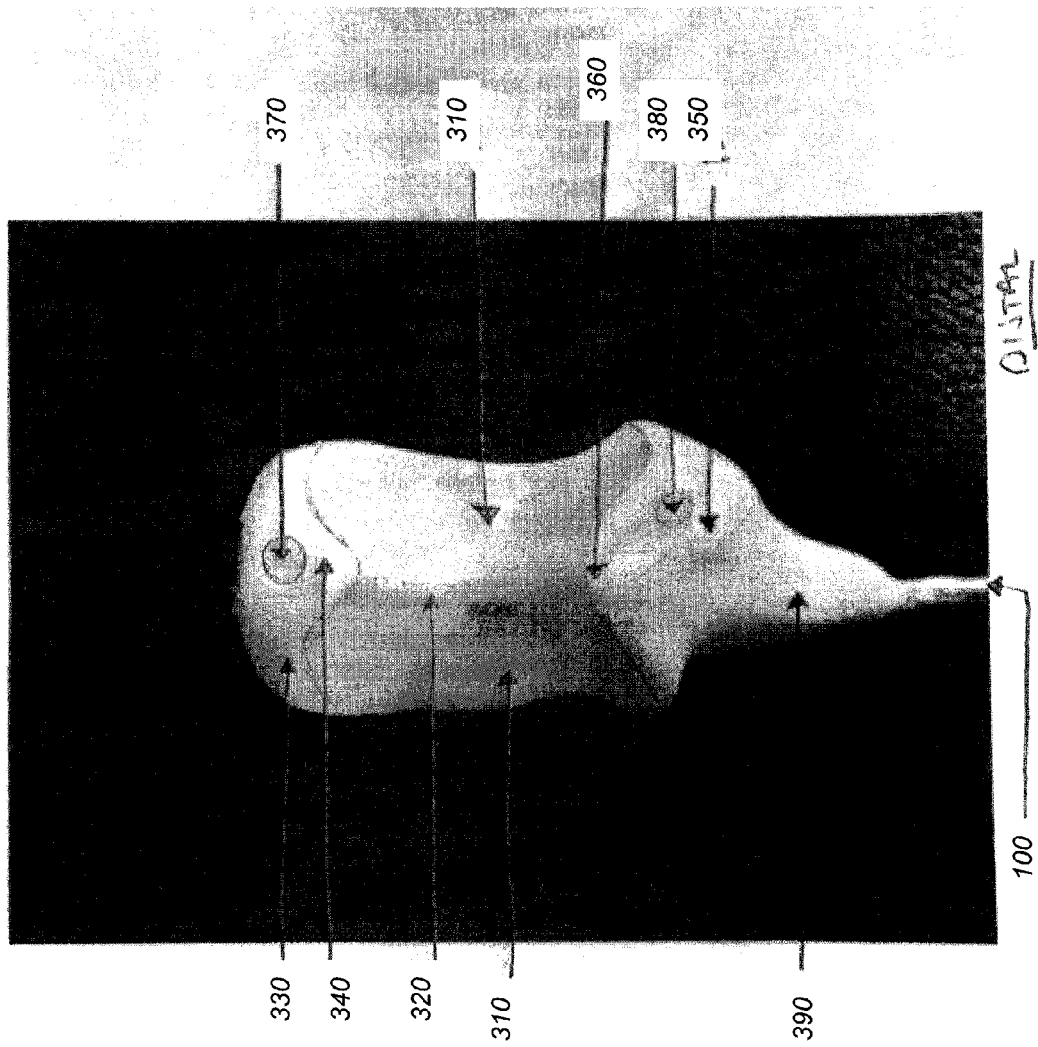
FIG. 3 is the ulnar component which provides an articulating surface for the humeral component of FIG. 2b.

Referring to FIG. 3, an anterior view of an ulnar component 300 is shown. The articular surface 310 is a mirror image of the distal articular surface 122 of the humeral component 100 and is divided by a ridge 320. The articular surface 310 compliments the medial trochlea 110 of FIG. 2a. That is to say that they have the same radius of curvature. The ridge 320 matches the groove 120 of FIG. 2a. That is to say that the ridge fits into the groove. The olecranon 330 is seen in the proximal portion of the component 300. It comes to a point or process 340. Distal to the articular surface is the coronoid 350. The coronoid has a point or process 360. The olecranon process 340 has a central olecranon tunnel 370. The coronoid process 360 also has a central coronoid tunnel 380. The coronoid tunnel 380 and the olecranon tunnel 370 are of substantially equal diameter and are oriented obliquely. Distal to the coronoid 350, the component includes a taper 390 which is configured to accept the central ulnar rod 200.

Figure 4:
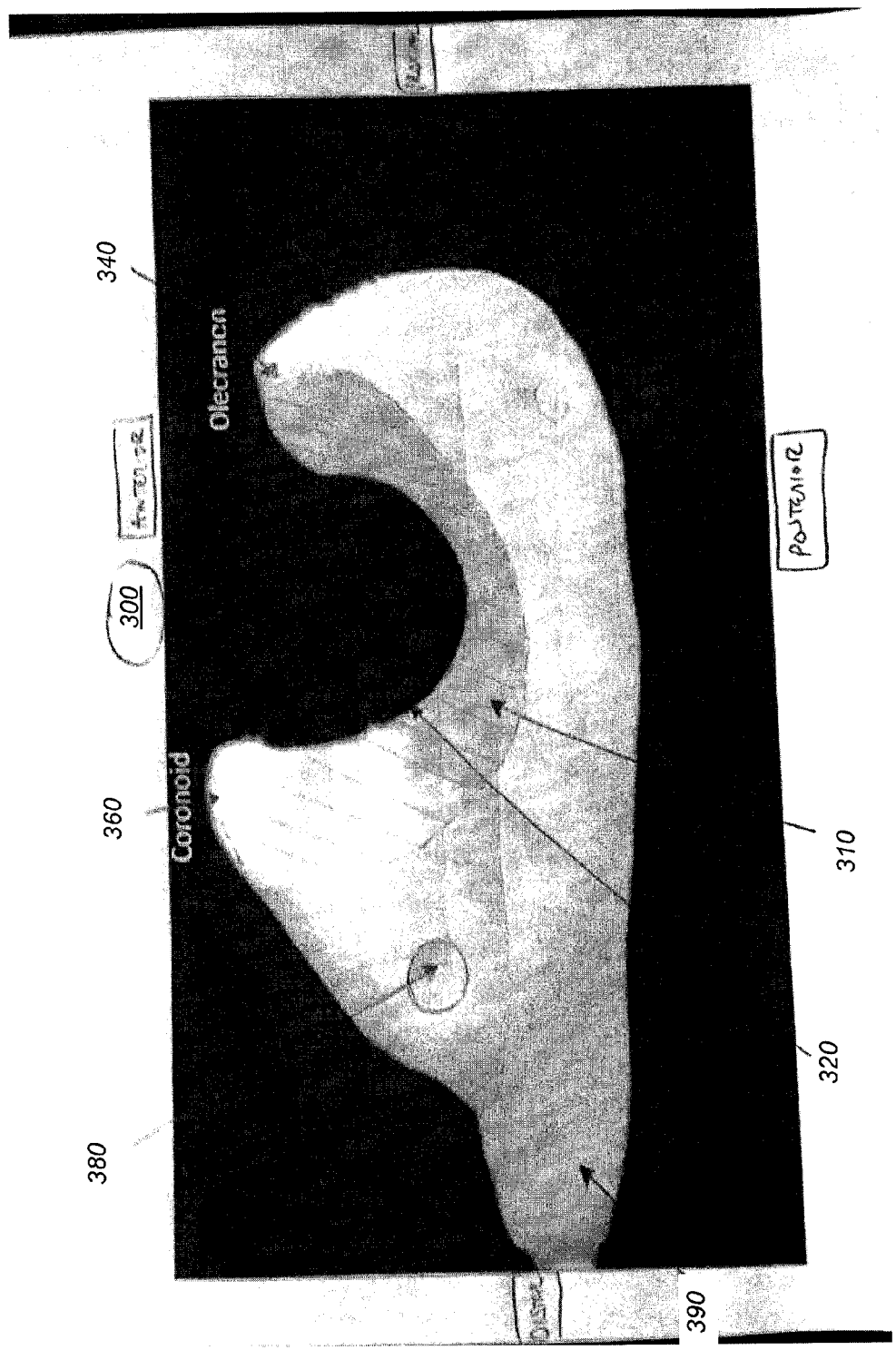
FIG. 4 is a lateral projection of the ulnar component.

Referring to FIG. 4, a lateral perspective of the ulnar component 300 is shown. The coronoid process 360 is slightly higher or more anterior than the olecranon process 340. The shorter or more posterior olecranon process 340 allows for better extension of the linked components. The articular surface 310 is shaded. Only one side of the articular surface 310 is shown in FIG. 4. It is noted that the articulated surface 310 is mirrored on the opposite side of the ulnar component 300. The articular surface 310 slopes to a point or ridge 320, which divides the ulnar component 300 in half. In some examples, the exit to the coronoid tunnel 380 exits at least 5 mm from the articular surface 310. Distal to the coronoid, the component includes a taper 390 to allow for insertion into the native ulnar canal.

Figure 5:
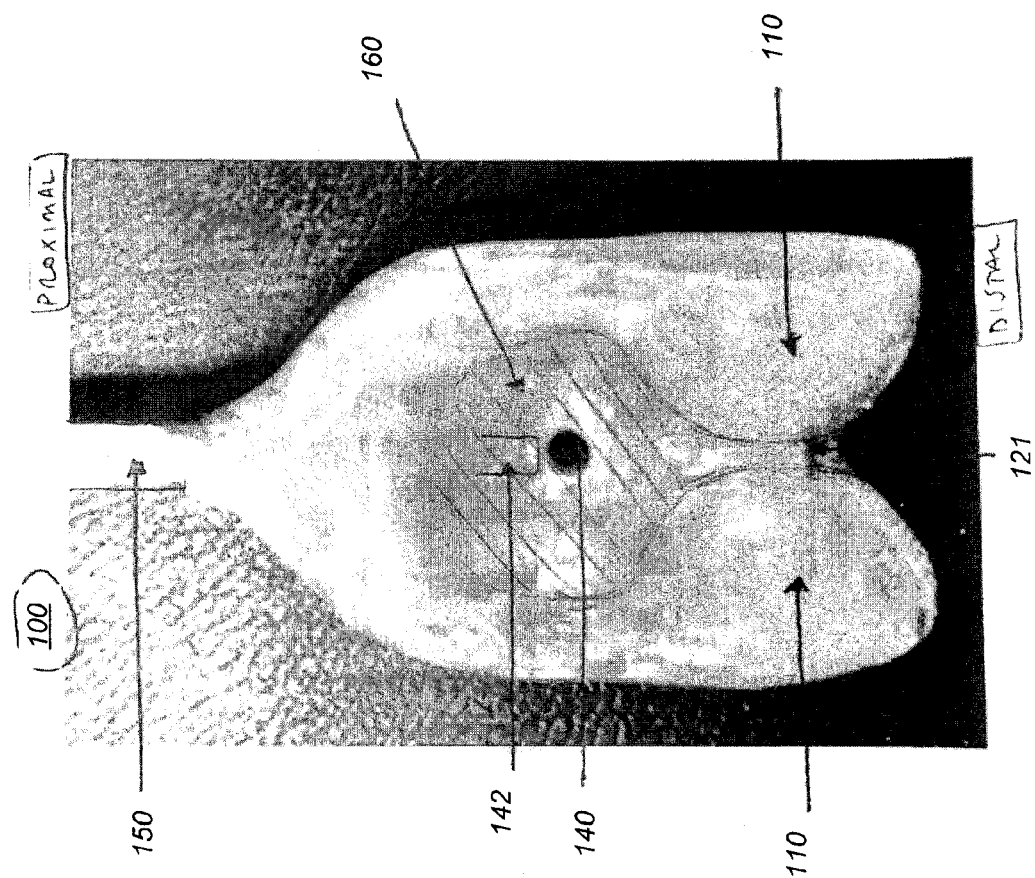
FIG. 5 is a perspective view of the humeral tunnel.

Referring to FIG. 5, an anterior view of the humeral component 100 is shown where the humeral component 100 is made from antibiotic bone cement. The distal articular surface is made from fused mirror images of the medial trochlea 110. The articular surface of the fused mirror images of the medial trochlea 110 is divided by a groove 121, which accepts the ridge 320 of the ulnar component of FIG. 4. The humeral component 100 has a central humeral tunnel 140 proximal to the articular surface of the fused mirror images of the medial trochlea 110 and the groove 121. The humeral rod 150 ends just proximal to the central humeral tunnel 140, at point 142. The shaded area 160 represents the thinnest portion of the component, which, in some examples, is only 2 mm thick near the central humeral tunnel 140. The shaded area 160 is thin and recessed to accept the tip of the coronoid process 360 of FIG. 6b during elbow flexion.

Figures 6A, 6B:
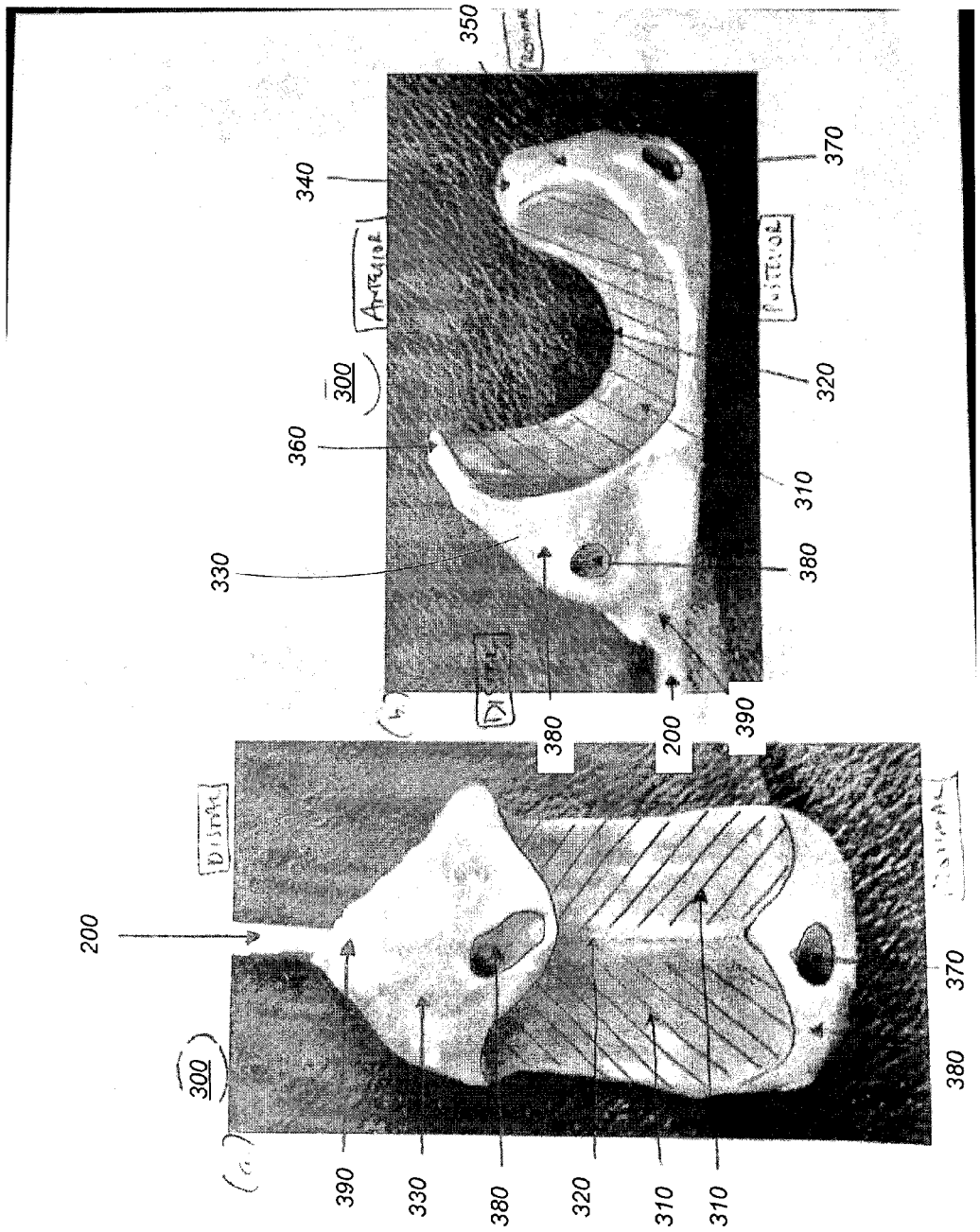

Referring to FIG. 6a, an anterior view of the ulnar component 300 shows the ulnar component 300 made from antibiotic bone cement. The shaded area 310 is a mirror image divided by a ridge 320 and represents the articular surface for the distal end of the humeral component. Distally, the coronoid process 330, tapers 390 into the ulnar rod 200. At the tip of the coronoid process 360 is the entrance to the central coronoid tunnel 380. The coronoid tunnel 380 is oriented obliquely to exit on the posterior side of the coronoid process 360. Proximally the central olecranon tunnel 370, is located at the tip of the olecranon process 340.

Referring to FIG. 6b, a lateral perspective of the ulnar component 300 shows the ulnar component 300 made from antibiotic bone cement. The shaded area 310 represents the articular surface and corresponds to the articular surface 310 of FIG. 6a. The ridge 320 represents a peak between the two identical sides of the articular surface 310. The ridge 320 corresponds to the ridge 320 of FIG. 6a. Distally the coronoid process 360 tapers 390 into the ulnar rod 200. The tip of the coronoid process 360 represents the starting point for the coronoid tunnel, which exits posterior and distal to the coronoid process 360. The tip of the olecranon process 340 represents the starting point for the olecranon tunnel, which exits posterior to the olecranon process 340.

Figure 7:
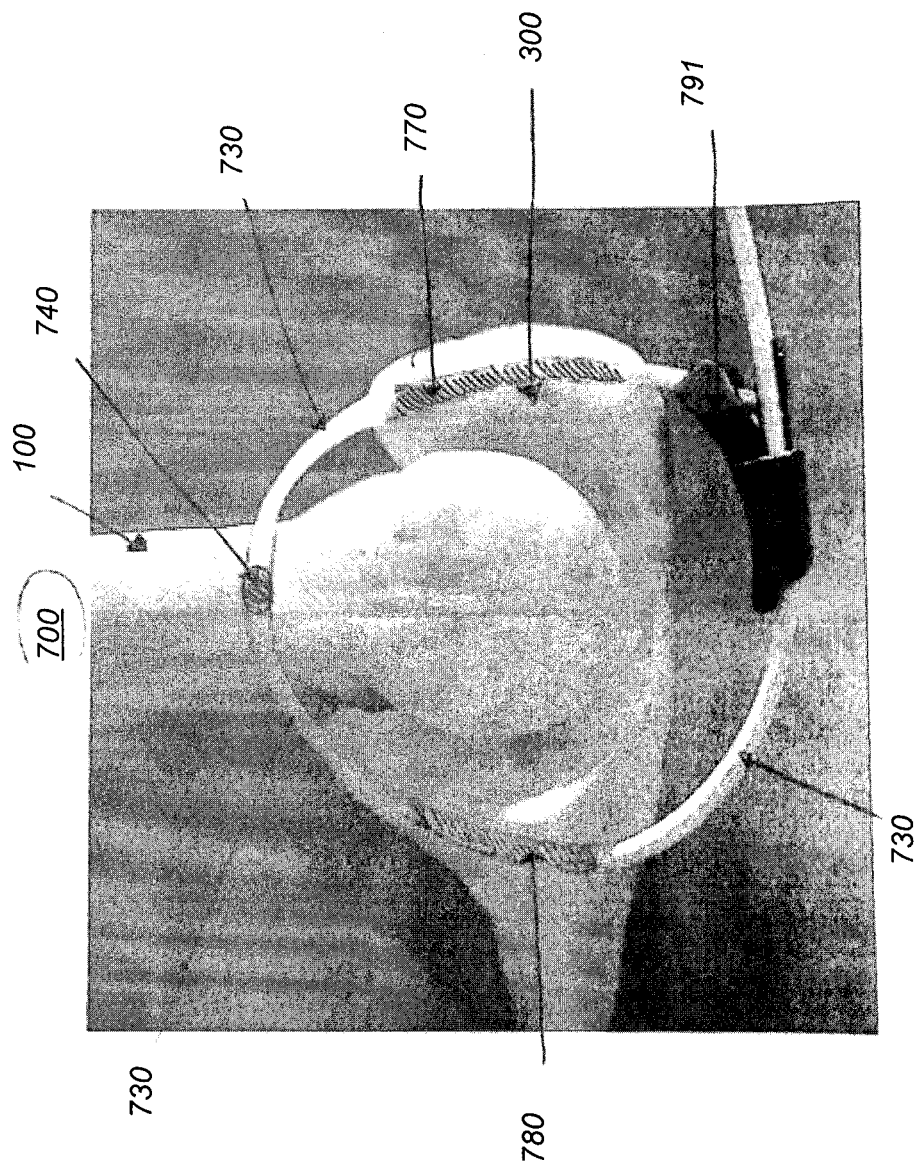
FIG. 7 illustrates the ulnar and humeral components linked together by a tie. The linkage device forms a circular pattern.

Referring to FIG. 7, a lateral perspective 700 of the linked humeral component 100 and ulnar component 300 is shown. The components are linked with a tie 730, which makes a circular pattern through the central axis of the components. It is noted that the term 'tie' relates to any type of element which can be used to fasten or tie something. Examples of ties include but are not limited to ropes, zip ties, cables, threads, strings, wires, and so on. The tie 730 passes through the olecranon tunnel 770 followed by the humeral tunnel 740, and finally the coronoid tunnel 780 of the ulna before passing through a clip 791.

Figure 8:
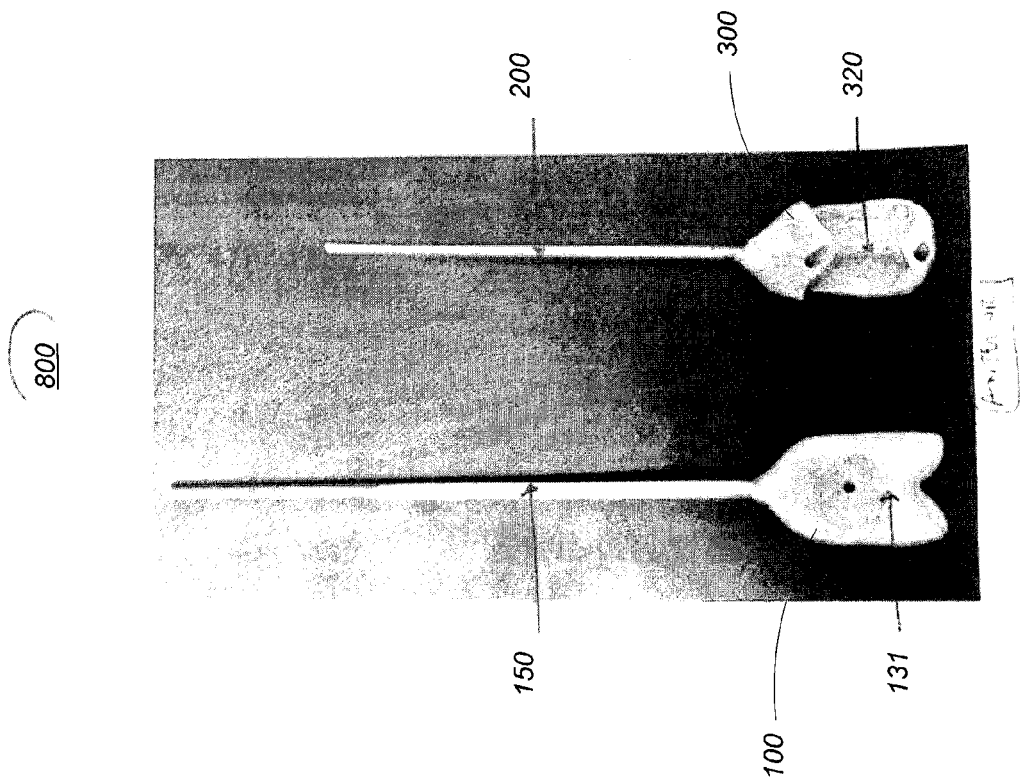
FIG. 8 illustrates the intramedullary rods in the central axis of the humeral and ulnar components.

Referring to FIG. 8, an anterior perspective 800 of the humeral component 100 and the ulnar component 300 shows the components 100, 300 made from antibiotic bone cement. The humeral rod 150 is located centrally within the body 131 of the humeral component. In some examples, the humeral rod 150 has a diameter of 3/16th of an inch. The ulnar rod 200 is located centrally within the ulnar component 300. In some examples, the ulnar rod 200 has a diameter of 1/8th of an inch.

Figures 9A, 9B:
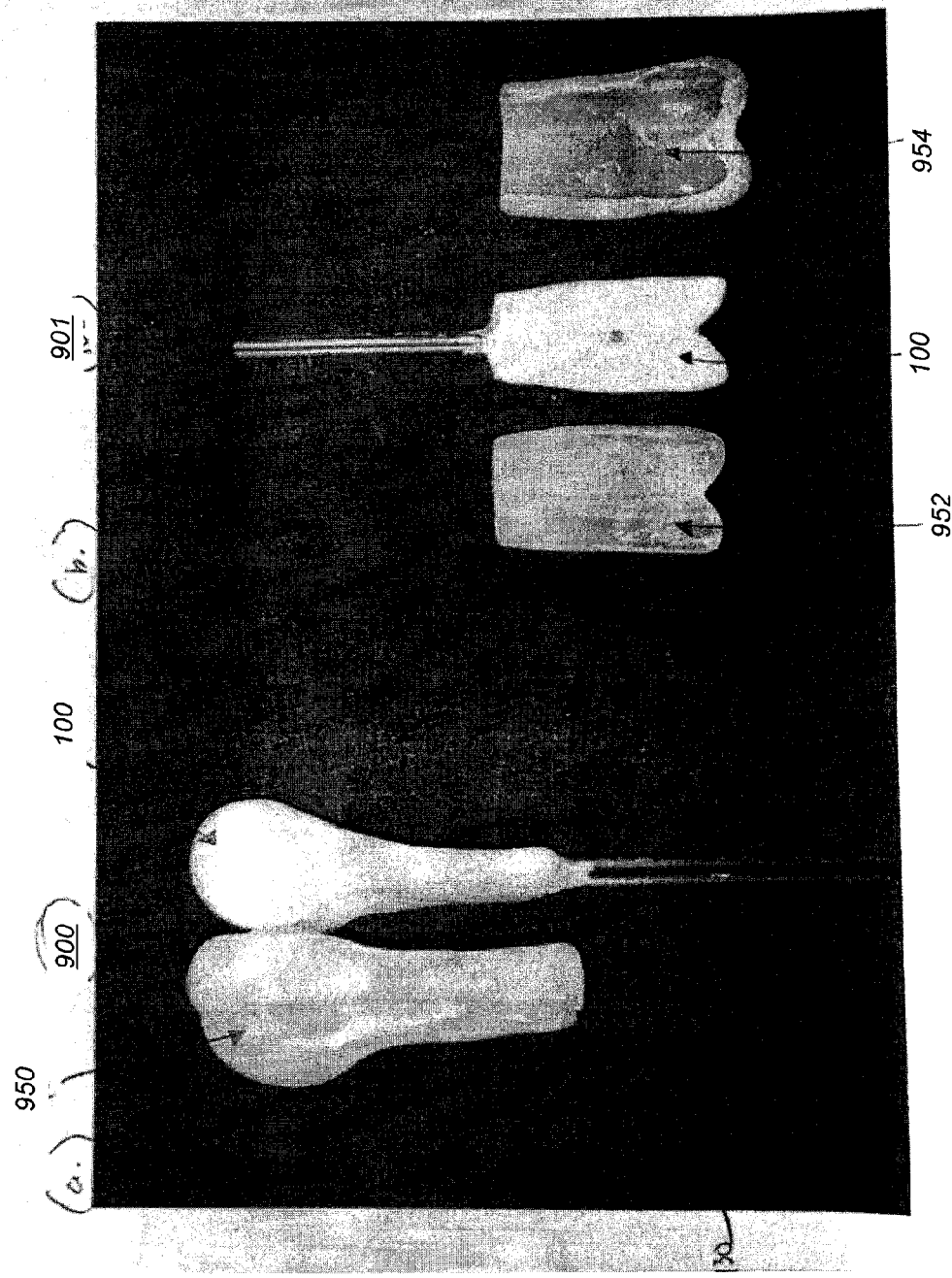
FIG. 9a is a lateral perspective of the humeral component and its corresponding plastic mold.
FIG. 9b is an anterior perspective of the humeral component with the two part plastic mold opened on either side.

Referring to FIG. 9a, a lateral perspective view 900 of the humeral component 100 and a humeral mold 950 is shown. In some examples, cement is poured into the mold 950 at the proximal open end 930 of the humeral mold 950.

Referring to FIG. 9b, an anterior perspective view 901 of the humeral component 100 is shown. The humeral component 100 is pictured with the mold 950 separated into two parts 952, 954. The two parts of the mold 950 include an anterior shell 952 which clips into a posterior shell 954 to form the completed mold 950 of FIG. 9a.

Figures 10A, 10B:
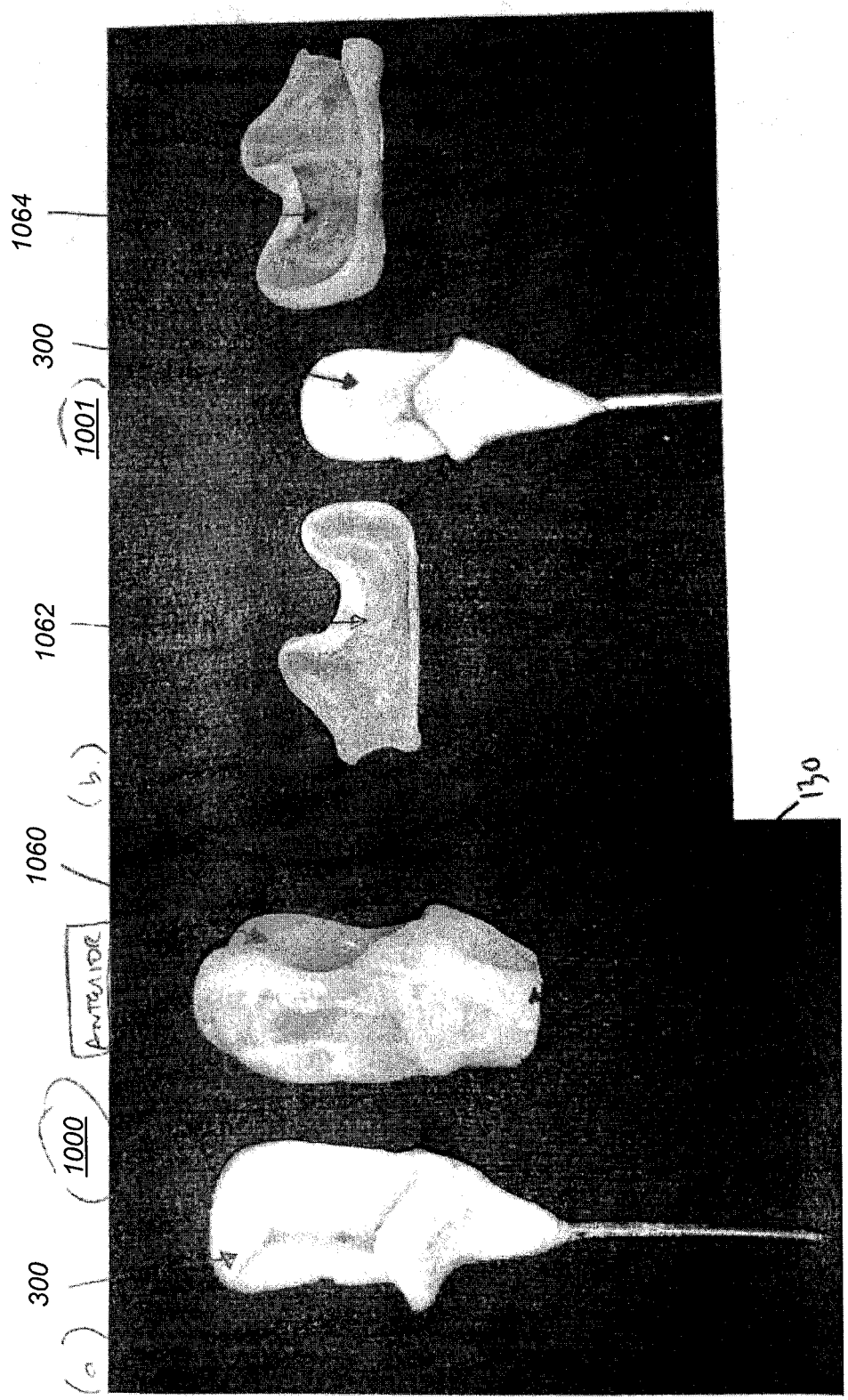
FIG. 10a is an anterior perspective of the ulnar component and its corresponding plastic mold
FIG. 10b is an anterior perspective of the ulnar component with the two part plastic mold opened on either side.

Referring to FIG. 10a, an anterior view 1000 of the ulnar component 300 and the ulnar mold 1060 is shown. In some examples, cement is poured into the mold 1060 at a distal open end 1030 of the ulnar mold 1060.

Referring to FIG. 10b, a perspective view 1001 of the ulnar component 300 is pictured along side the ulnar mold 1060 which is separated into two parts 1062, 1064. The two-part ulnar mold 1062, 1064 clips together along the sagittal plane of the ulnar mold 1060 to for the ulnar mold 106 of FIG. 10a.

It is to be understood that the foregoing description is intended to illustrate and not to limit the scope of the invention, which is defined by the scope of the appended claims. Other embodiments are within the scope of the following claims.

What is claimed is:

1. An articulable elbow spacer comprising:
   a humeral component including
      a proximal end having a rod for insertion into a humeral canal;
      a distal end including a first joint member, the first joint member including antibiotic cement and one or more tunnels;
   an ulnar component including
      a proximal end including a second joint member, the second joint member including antibiotic cement and including one or more tunnels, and configured to receive the first joint member; and
      a distal end having a rod for insertion into an ulnar canal;
   a tie for linking the humeral component to the ulnar component, the tie configured for insertion into the one or more tunnels of the first joint member and the one or more tunnels of the second joint member.

2. The articulable elbow spacer of claim 1 wherein the first joint member includes a groove and the second joint member includes a ridge configured to be received by the groove.

3. The articulable elbow spacer of claim 2 wherein the first joint member includes a first medial trochlea shaped portion fused to a second medial trochlea shaped portion, the first medial trochlea shaped portion and the second medial trochlea shaped portion defining the groove, wherein the first medial trochlea shaped portion is a reflection of the second medial trochlea shaped portion.

4. The articulable elbow spacer of claim 2 wherein the groove is a substantially V-shaped groove.

5. The articulable elbow spacer of claim 2 wherein the groove includes an inner surface having a first inner surface wall and a second inner surface wall opposing the first inner surface wall, wherein the first inner surface wall has a convex shape and the second inner surface wall has a convex shape.

6. The articulable elbow spacer of claim 1 wherein the ulnar component includes a coronoid process and an olecranon process for limiting a range of articulation of the articulable elbow spacer.

7. The articulable elbow spacer of claim 6 wherein the coronoid process protrudes further from the ulnar component in an anterior direction than the olecranon process.

8. The articulable elbow spacer of claim 1 wherein the tie has a circular shape and the one or more tunnels of the distal end of the joint member and the one or more tunnels of the proximal end of the second joint member form a circular tunnel pattern configured to receive the tie.

9. The articulable elbow spacer of claim 1 wherein the humeral component and the ulnar component form a ginglymus hinge.

10. The articulable elbow spacer of claim 1 wherein the first joint member includes a tapered portion tapering along a direction from the distal end of the humeral component to the proximal end of the humeral component.

11. The articulable elbow spacer of claim 1 wherein the second joint member includes a tapered portion tapering along a direction from the proximal end of the ulnar component to the distal end of the ulnar component.

12. The articulable elbow spacer of claim 1 wherein a thinnest portion of the humeral component has a thickness in a range of 1 mm to 3 mm.

13. The articulable elbow spacer of claim 12 wherein the thinnest portion of the humeral component has a thickness of 2 mm.

14. The articulable elbow spacer of claim 1 wherein the rod for insertion into the humeral canal has a diameter of 3/16 of an inch.

15. The articulable elbow spacer of claim 1 wherein the rod for insertion into the ulnar canal has a diameter of 1/8 of an inch.

* * * * *